(12) United States Patent
Hotamisligil

(10) Patent No.: US 7,056,662 B2
(45) Date of Patent: Jun. 6, 2006

(54) METHOD OF DIAGNOSING A RISK OF DEVELOPING INSULIN RESISTANCE

(75) Inventor: Gokhan S. Hotamisligil, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 348 days.

(21) Appl. No.: 09/788,074

(22) Filed: Feb. 16, 2001

(65) Prior Publication Data

US 2001/0044110 A1    Nov. 22, 2001

Related U.S. Application Data

(60) Provisional application No. 60/183,106, filed on Feb. 17, 2000.

(51) Int. Cl.
| | |
|---|---|
| C12Q 1/68 | (2006.01) |
| C12P 19/34 | (2006.01) |
| C07H 21/02 | (2006.01) |
| C07H 21/04 | (2006.01) |

(52) U.S. Cl. .................. 435/6; 435/91.1; 536/23.1; 536/23.5; 536/24.31

(58) Field of Classification Search ............... 536/23.1, 536/23.5, 24.31, 24.33, 24.3; 530/300; 424/198.1; 435/6, 91.1, 325, 352, 354, 366, 375, 91.2, 435/91.21, 91.51

See application file for complete search history.

(56) References Cited

FOREIGN PATENT DOCUMENTS

WO    WO 00/47734    8/2000

OTHER PUBLICATIONS

R. E. Pratley et al., The role of impaired early insulin secretion in the pathogenesis of Type II diabetes mellitus, DIABETOLOGIA (2001) 44: pp. 929-945.*

Kane, C.D., et al., Expression, Purification, and Ligand-Binding Analysis of Recombinant Keratinocyte Lipid-Binding Protein (MAL-1), and Intracellular Lipid-Binding Protein Found Overexpressed in Neoplastic Skin Cells, *Biochemistry*, vol. 35, No. 9, pps. 2894-2900, 1996.

Hertzel A.V., et al., Cloning and Chromosomal Location of the Murine *Keratinnocyte Lipid-Binging Protein* Gene, *Gene*, vol. 221 (2), pp. 235-243, 1998.

Crooke, "Therapeutic Application of Oligonucleotides," Annu. Rev. Pharmacol. Toxicol. 32,329-346, 1992.

Dolnick, "Antisense Agents in Pharmacology," Biochem. Pharmacol. 40:671-675, 1990.

Genbank™ Accession No. AFO61015.

Genbank™ Accession No. M94856.

Hertzel et al., "Cloning and chromosomal location of the murine keratinocyte lipid-binding protein gene," Gene, 221(2):253-43. (1998).

Hotamisligil et al., "Uncoupling of obesity from insulin resistance through a targeted mutation in aP2, the adipocyte fatty acid binding protein," Science, 274(5291) pp. 1377-1379 (1996).

Kane et al., "Expression, Purification, and Ligand-binding Analysis of Recombinant Keratinocyte Lipid-binding Protein (mal-I), an Intracellular Lipid-binding Protein Found Overexpressed in neoplastic Skin Cells," Biochemistry, 35(9): 2898-2900. 1996.

Le Doan et al., "Antisense Oligonucleotides as Potential Antiviral and Anticancer Agents," Bull. Cancer 76:849-852, 1989.

Melani et al., "Inhibition of Proliferation by-c-*myb* Antisense Oligodeoxynucleotides in Colon Adenocarcinoma Cell Lines That Express c-*myb*," 1991, Cancer Res. 51:2897-2901.

Scheja et al., "The adipocyte fatty acid-binding protein (aP2) as a cofactor of lipolysis in cultured adipocytes and in vivo," Diabetes, vol. 48 No. Suppl. 1, pp. A259-A260. (1990).

Shaughnessy et al., "Adipocyte metabolism in adipocyte fatty acid binding protein knockout mice (aP2-/-) after short-term high-fat feeding; functional compensation by keratinocyte! fatty acid binding protein," Diabetes, 49(6):904-11. (May. 2000).

* cited by examiner

*Primary Examiner*—Jane Zara
(74) *Attorney, Agent, or Firm*—Mintz Levin; Ingrid A. Beattie

(57) ABSTRACT

The invention provides compositions and methods of inhibiting Mal1 expression or function to treat lipid metabolisms disorders.

6 Claims, 7 Drawing Sheets

METHOD OF DIAGNOSING A RISK OF DEVELOPING INSULIN RESISTANCE

RELATED APPLICATIONS

This application claims priority to provisional application U.S. Ser. No. 60/183,106, filed Feb. 17, 2000.

STATEMENT AS TO FEDERALLY FUNDED RESEARCH

This invention was supported by National Institutes of Health Grant No. DK09823. The government has certain rights in the invention.

TECHNICAL FIELD

This invention relates to lipid metabolism disorders.

BACKGROUND

Obesity, insulin resistance, diabetes, dyslipidemia, and atherosclerosis are significant public health concerns. Advances in molecular genetics of cardiovascular disease have enabled the identification of individuals at high cardiovascular risk. Researchers continue to search for genetic risk factors for diabetes and atherosclerosis. Although hyperinsulinemia has been linked with cardiovascular disease and atherosclerosis, the connection between these pathological condition is not understood.

SUMMARY

The invention is based on the discovery that decreasing Mal1 (also called keratinocyte fatty acid binding protein) expression prevents or inhibits the development of obesity, insulin resistance, diabetes, dyslipidemia, and atherosclerosis. Accordingly, the invention features a method of preventing or inhibiting such conditions by administering to a mammal, e.g., a human patient who has been identified as suffering from or at risk of developing one or more of the above-listed pathologies, a compound that reduces expression or activity of Mal1. Preferably, the compound inhibits transcription of endogenous Mal1. The compound binds to a cis-acting regulatory sequence of the Mal1 gene and decreases Mal1 transcription. Alternatively, the compound inhibits translation of Mal1 mRNA into a Mal1 gene product, e.g., an antisense nucleic acid. Antisense therapy is carried out by administering a single stranded nucleic acid complementary at least a portion of Mal1 mRNA. In another example, the antisense nucleic acid is a DNA template operatively linked to a promoter (e.g., a macrophage-specific promoter), and the transcription of the DNA template yields an antisense nucleic acid product which is complementary to an mRNA encoding an Mal1 polypeptide. For example, an antisense nucleic acid is complementary to sequences in exon 1 of a Mal1 gene. Nucleic acids complementary to all or part of a Mal1 coding sequence are used to inhibit Mal1 expression. The nucleic acid is at least 10 nucleotides in length (more preferably at least 20, 30, 40, 50 nucleotides in length) and is complementary at least a 10 nucleotide stretch of a mouse or human Mal1 cDNA

TABLE 1

Amino acid sequence of mouse Mal1 (keratinocyte fatty acid binding protein)

MASLKDLEGKWRLMESHGFEEYMKELGVGLALRKMAAMAKPDCIITCDGN
NITVKTESTVKTTVFSCNLGEKLFDETTADGRKTETVCTFQDGALVQHQ
QWDGKESTITRKLKDGKMIVECVMNNATCTRVYEKVQ (SEQ ID NO:1;GENBANK ™ Accession No. AFO61015)

TABLE 2

Nucleotide sequence of mouse Mal1 (kerotinocyte fatty acid binding protein)

```
   1 aatgggagca acatgctagc tatgcaggtc ggtgagtgag tgagtgagtg acaagaggct
  61 ggccagtggg atgataagga atgaatcctt gcttatcatt gtacaaatta cgtcattttc
 121 catacccaca ggagtaggac tggctcttag gaagatggct gccatggcca agccagactg
 181 tatcattacg tgtgatggca acaacatcac ggtcaaaacc gagagcacag tgaagacgac
 241 tgtgttctct tgtaacctgg gagagaagtt tgatgaaacg acagctgatg gcagaaaaac
 301 tgaggtcagc tacaacatac tgtgaagcga cagaagcttc tagatttaca gattaaattg
 361 cattaacaat gtctgtactt actgccaagg gctgactgaa aaaactactt tatggagttg
 421 acttttgata aattagtaaa agtcccagga ctaagaaatg aagacatctt atgagtttct
 481 agatcgaaaa gcacatagtt gtattgtgaa caaaatcagt atgatggggt ggagttcaga
 541 gagggaaagg cgaagacttg ttggagtggt gtgggtcctg ggggttcctt cactttggaa
 601 gatgatgaac taactaccct gtattttgc agacggtctg caccttccaa gacggtgccc
 661 tggtccagca ccagcaatgg gacgggaagg agagcacgat aacaagaaaa ctgaaggatg
 721 ggaagatgat cgtggtgagc atcaaagcac tggcaccatg ctgggattgg gcctgcagcc
 781 acagttgtca taaccacttc gggtcattgg ttctttaaca agagaaggaa acttaggagg
 841 acaatactga aaataacaag ttagaaacga gagtcctcat tgctgaggca gcccttgtgg
 901 ggacggagaa gtgatgggat cccaggatgt ggctgcagca gagcctgaga gctggcaggc
 961 caccgagcag ccctctcctg gtacattgat ttaagtaagg gatatttgcc aaaacacatg
1021 aataatttag agatcatatc cagtgcttta gtctgcaggg cagcaaatat acatataaac
1081 aaaacagcag ctctaggtct tcttgagttt gaatcctgag atgtggtttt tctgttaggt
1141 tggttacaag cgtttatagg attctgccca caacacatgc tctgaaatgt acagttggcc
1201 tgagactcta tctttcttct cctaggagtg tgtcatgaac aatgccacct gcactcgggt
1261 ctatgagaag gtgcaatga
```

(SEQ ID NO:2 ;GENBANK ™ Accession No. AFO61015; for cDNA, join nucleotides 569..647,132..304,633..734, and 1226..1279)

TABLE 3

Amino acid sequence of human Mal1
(kerotinocyte fatty acid binding protein)

MATVQQLEGRWRLVDSKGFDEYMKELGVGIALRKMGAMAKPDCIITCD
GKNLTIKTESTLKTTQFSCTLGEKFEETTADGRKTQTVCNFTDGALVQ
HQEWDGKESTITRKLKDGKLVVECVMNNVTCTRIYEKVE (SEQ ID NO:3 ;GENBANK ™ Accession No. M94856)

TABLE 4

Nucleotide sequence of human Mal1 (kerotinocyte fatty acid binding protein)

```
  1 accgccgacg cagaccccte tctgcacgcc agcccgcccg cacccaccat ggccacagtt
 61 cagcagctgg aaggaagatg gcgcctggtg gacagcaaag gctttgatga atacatgaag
121 gagctaggag tgggaatagc tttgcgaaaa atgggcgcaa tggccaagcc agattgtatc
181 atcacttgtg atggtaaaaa cctcaccata aaaactgaga gcactttgaa aacaacacag
241 ttttcttgta ccctgggaga gaagtttgaa gaaccacag ctgatggcag aaaaactcag
301 actgtctgca actttacaga tggtgcattg gttcagcatc aggagtggga tgggaaggaa
361 agcacaataa caagaaaatt gaaagatggg aaattagtgg tggagtgtgt catgaacaat
421 gtcacctgta ctcggatcta tgaaaaagta gaataaaaat tccatcatca ctttggacag
481 gagttaatta agagaatgac caagctcagt tcaatgagca aatctccata ctgtttcttt
541 ctttttttt tcattactgt gttcaattat ctttatcata aacattttac atgcagctat
601 ttcaaagtgt gttggattaa ttaggatcat ccctttggtt aataaataaa tgtgtttgtg
661 ct
```

(SEQ ID NO:4;GENBANK ™ Accession No. M94856; cDNA spans nucleotides
49–456; polyA signal spans 645–650)

The Mal1 inhibitory compound is administered systemically or locally.

The invention also includes a method of preventing or inhibiting the development of obesity, insulin resistance, diabetes, dyslipidemia, and atherosclerosis by administering to a mammal a compound that reduces activity of Mal1. By "Mal1 activity" is meant fatty acid binding. The level of Mal1 activity is determined by measuring the level of circulating free fatty acids in a mammal. A reduction in the level of circulating free fatty acids indicates an inhibition of Mal1 activity.

The invention also includes a method of diagnosing individuals who are at risk of developing obesity, insulin resistance, diabetes, dyslipidemia, and atherosclerosis. An increase in patient Mal1 gene product or transcripts indicates that the patient is suffering from or at risk of developing one or more of the pathological conditions described above. A mutation in the Mal1 gene which leads to increased Mal1 production also indicates a predisposition to developing such conditions. Tissue samples to be tested include peripheral blood or cells (e.g., macrophages) derived from a blood sample, as well as solid tissue sample (e.g., adipose tissue).

Other features and advantages of the invention will be apparent from the description and drawings.

DETAILED DESCRIPTION

Fatty acid binding proteins (FABP) such as Mal1 or keratinocyte fatty acid binding protein) are members of a family of small cytoplasmic proteins which function to traffic lipid in the cell. The gene encoding Mal1, a member of the FABP family, was found to be upregulated in multistage skin carcinogeneis. The gene product is expressed in adipocytes as well as other cell types such as macrophages. In aP2-deficient mice, a compensatory increase in expression of Mal1 protein in adipose tissue was observed. To further determine the role of Mal1 in adipocyte biology and energy metabolism, mice which are homozygous for a targeted null mutation in the mal1 gene were generated.

Genetic ablation of Mal1 (keratinocyte fatty acid binding protein) results in decreased body weight, increased systemic insulin sensitivity, reduced glucose and insulin levels, reduced plasma triglyceride levels, reduced plasma cholesterol levels, and improved lipoprotein profiles (with increased HDL and decreased LDL). Mal1 knockout mice have reduced circulating lipids. Mal1 was found to be expressed in and developmentally regulated in macrophages. The data described herein indicate that inhibitors of Mal1 expression or activity are useful to treat obesity, insulin resistance, diabetes, hyperlipidemia, and atherosclerosis.

Mal-1-deficient Mice

Figure 1:
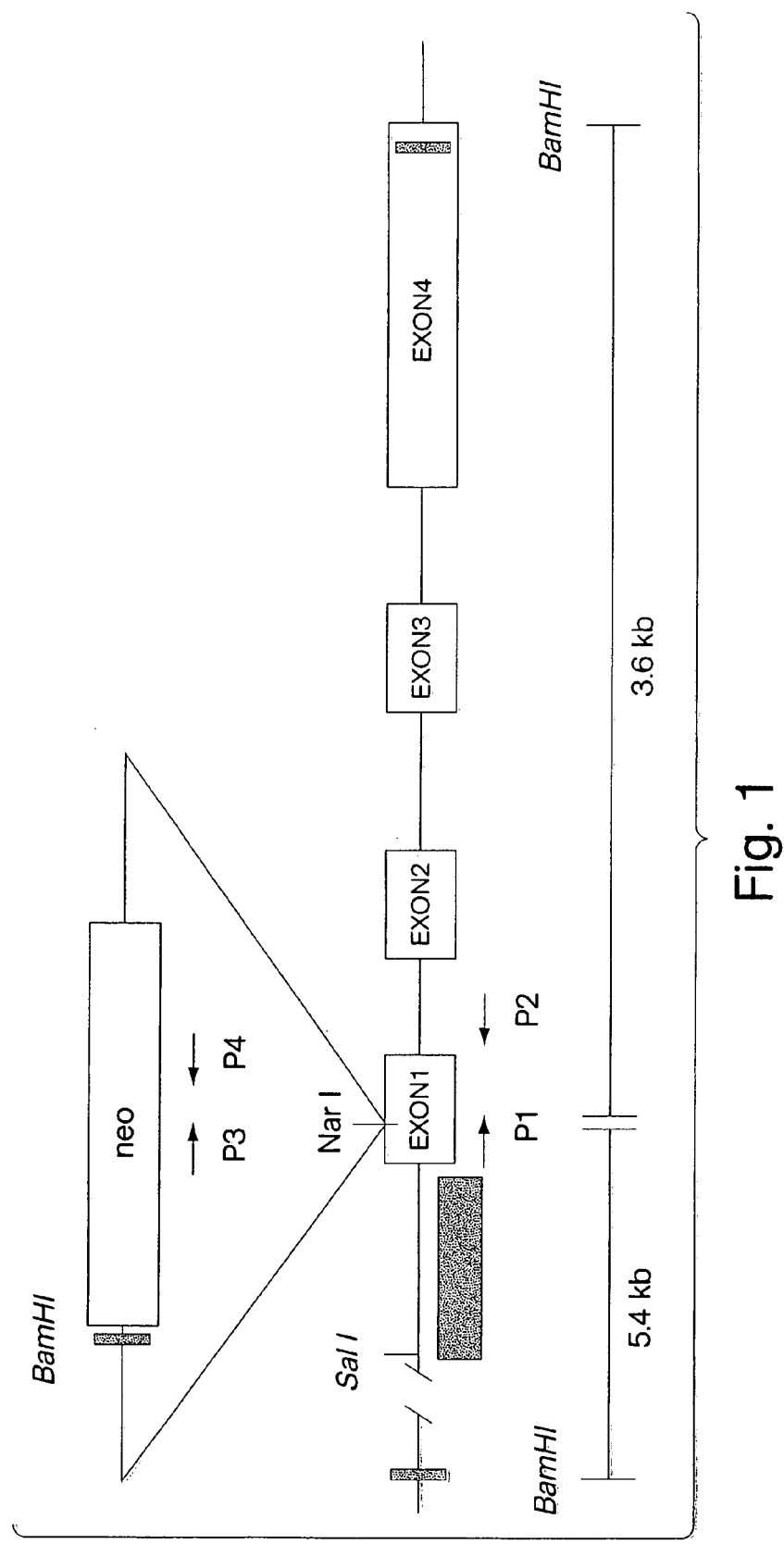
FIG. 1 is a diagram of the genomic structure of Mal-1-deficient mice and the deletion mutagenesis strategy used to generate the Mal-1-deficient mice.

The mal1 gene was targeted and a null mutation made using standard methods. The deletion strategy is shown in FIG. 1. Primers P1 and P2 were used to amplify the wild type allele, and primers P3 and P4 were used to amplify the targeted allele. Germline transmission of the targeted allele was followed by backcrossing five generations onto C57B16/J mice and sibling crosses to obtain homozygous null mice on an inbred background.

Figure 2:
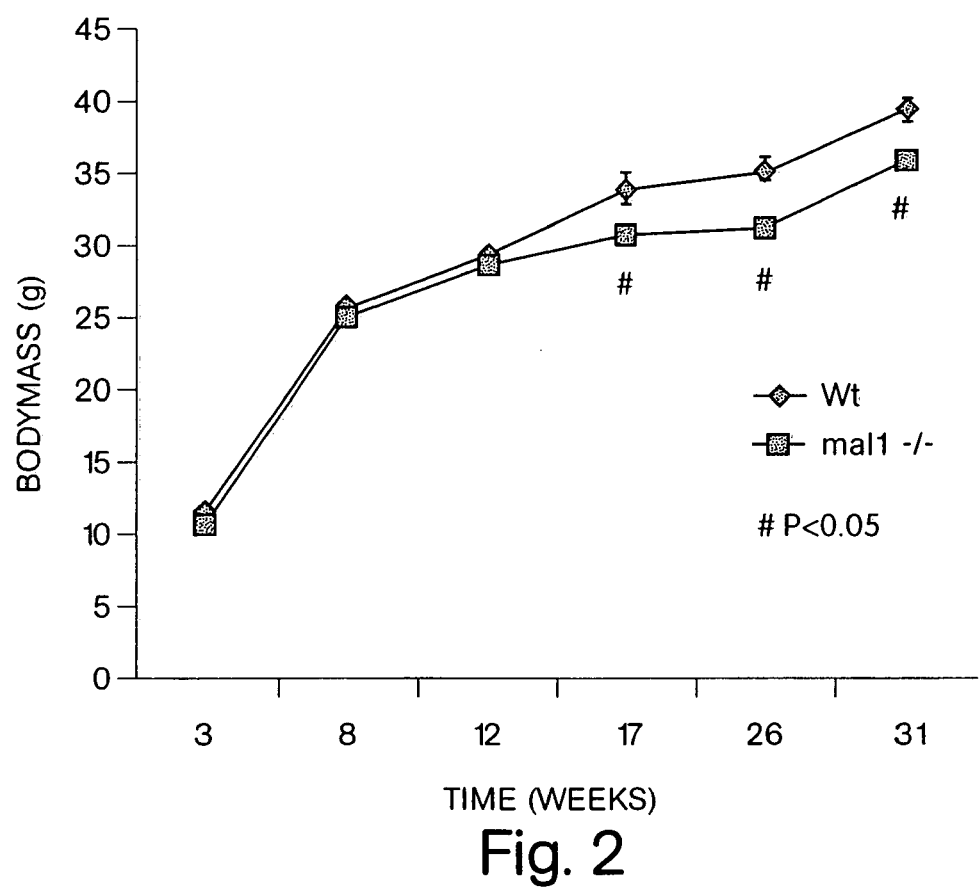
FIG. 2 is a line drawing showing growth curves of wild type mice compared to mal1-/-mice. Time (in weeks) is plotted on the x-axis, and body mass (in grams) is plotted on the y-axis.

Mal1-deficient mice are crossed with other knockout mice to determine the contribution of Mal1 in other disease models such as models for atherosclerosis or obesity. For example, double knockout mice are generated with have homozygous mutation in the Mal1 gene as well as another gene such as Ob/Ob, Tubby/Tubby, Db/Db, Fat/Fat, kka$^y$/kka$^y$. The date shown in FIG. 2 demonstrated that Mal1-deficient mice have reduced body fat. These data indicate that inhibiting expression of activity of Mal1 is useful to treat obesity.

Glucose Metabolism

Figure 3A:
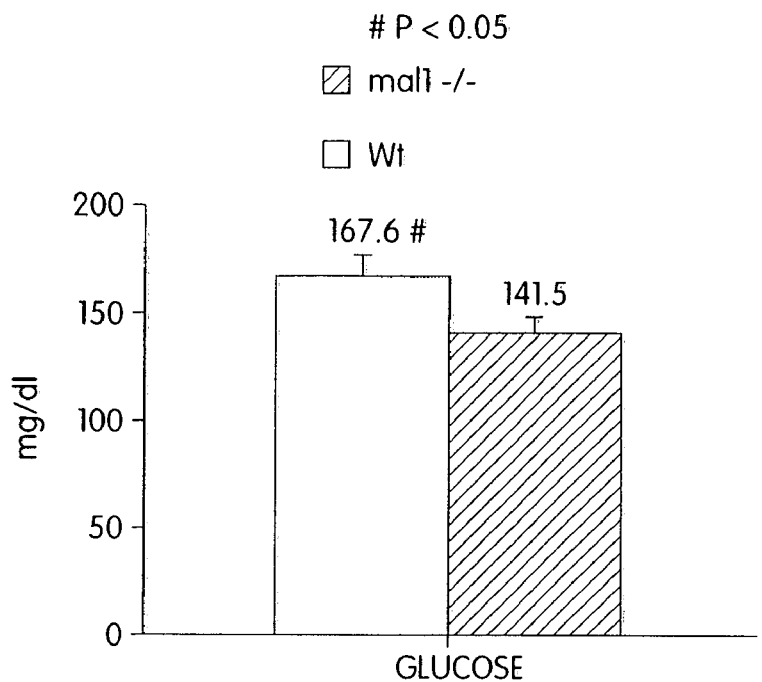
FIG. 3A is a bar graph showing plasma glucose levels in wild type and mal1-/-mice.
Figure 3B:
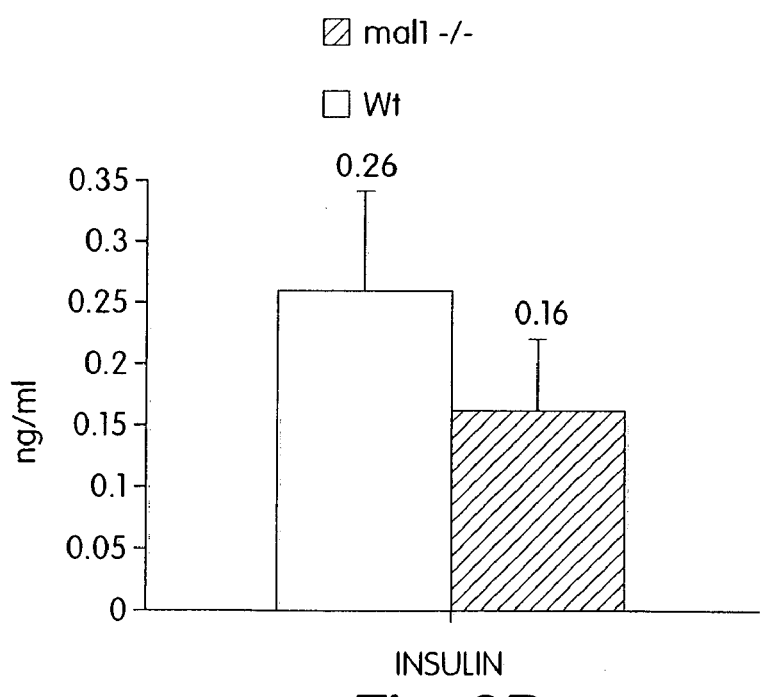
FIG. 3B is a bar graph showing plasma insulin levels in wild type and mal1-/-mice.
Figure 4:
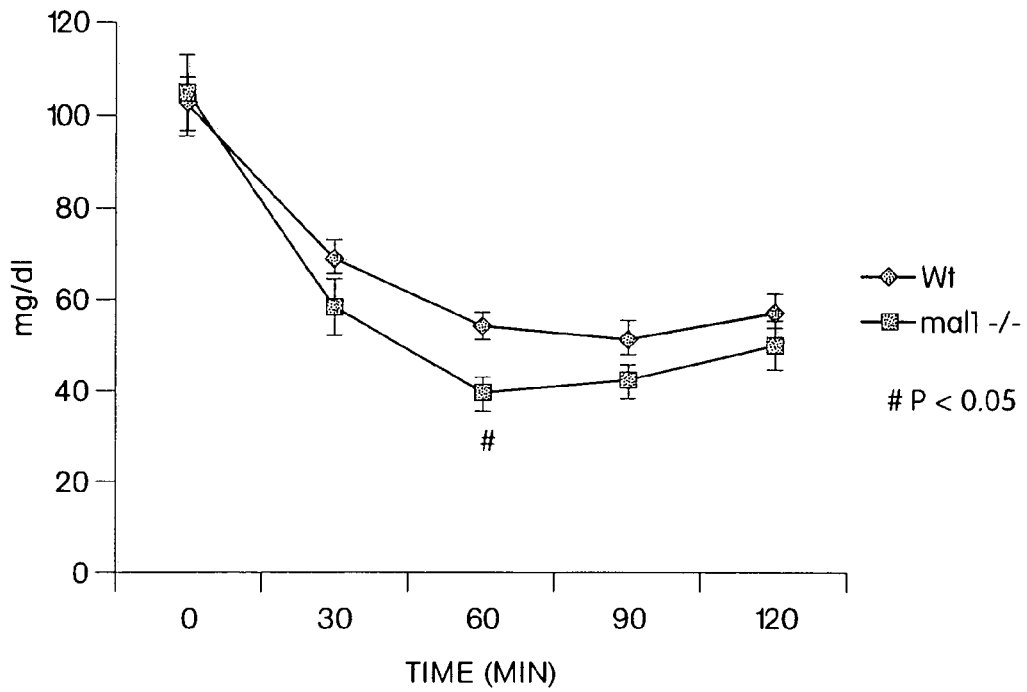
FIG. 4 is a line graph showing the rate of glucose metabolism in wild type and mal1-/-mice as measured using a standard insulin tolerance test
Figure 5:
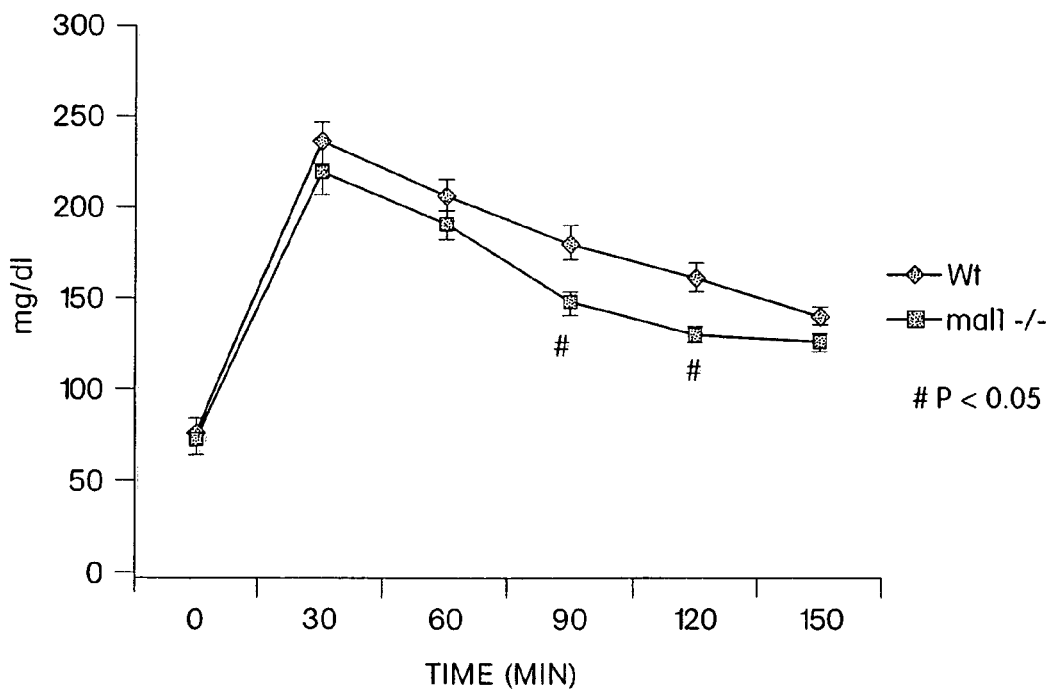
FIG. 5 is a line graph showing the rate of glucose metabolism in wild type and mal1-/-mice using a standard glucose tolerance test.

Blood sample were taken from wild type and mutant mice. Animals were followed for 7 months (Mal-deficient mice (n=8); wild type mice (n=7). Blood samples were collected after 24 hours of fasting in week 18 and 22 (Fasted State). For Postprandial state (after feeding), samples were collected at 1:00 a.m. after free access to food in week 26. The data depicted in FIGS. 3A–B demonstrates that Mal1 knockout mice have a lower plasma level of glucose and insulin compared to wild type mice using a standard plasma test. FIGS. 4 and 5 confirm these data using a standard insulsin tolerance test (ITT; FIG. 4) or a standard glucose tolerance test (GTT; FIG. 5). The data indicate that decreased Mal1 expression results in increased glucose sensitivity. Mal1-deficient mice were more capable of metabolizing ingested glucose and did so at a faster rate compared to wild type animals.

Lipid Metabolism

Figure 6:
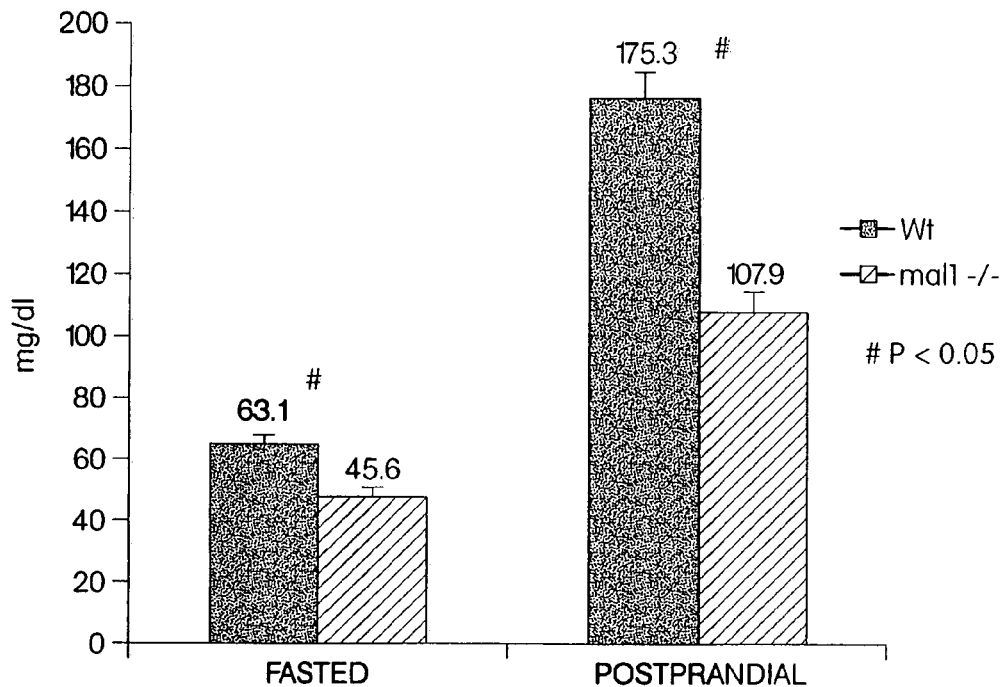
FIG. 6 is a bar graph showing plasma triglyceride levels in wild type and mal1-/-mice in a fasted state compared to a postprandial state.
Figure 7:
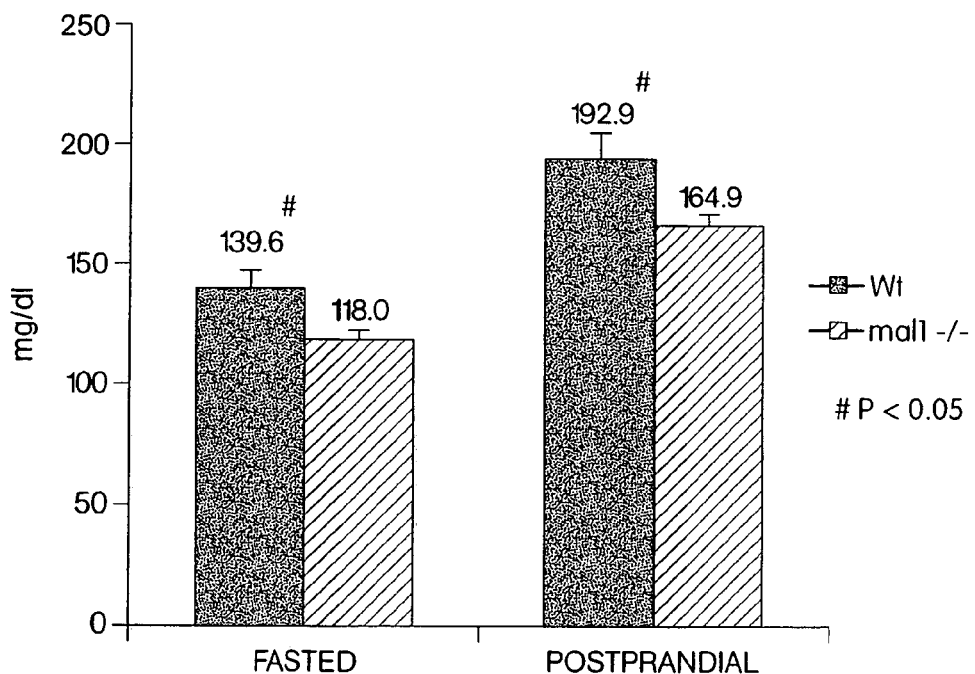
FIG. 7 is a bar graph showing plasma cholesterol levels in wild type and mal1-/-mice in a fasted state compared to a postprandial state.
Figure 8:
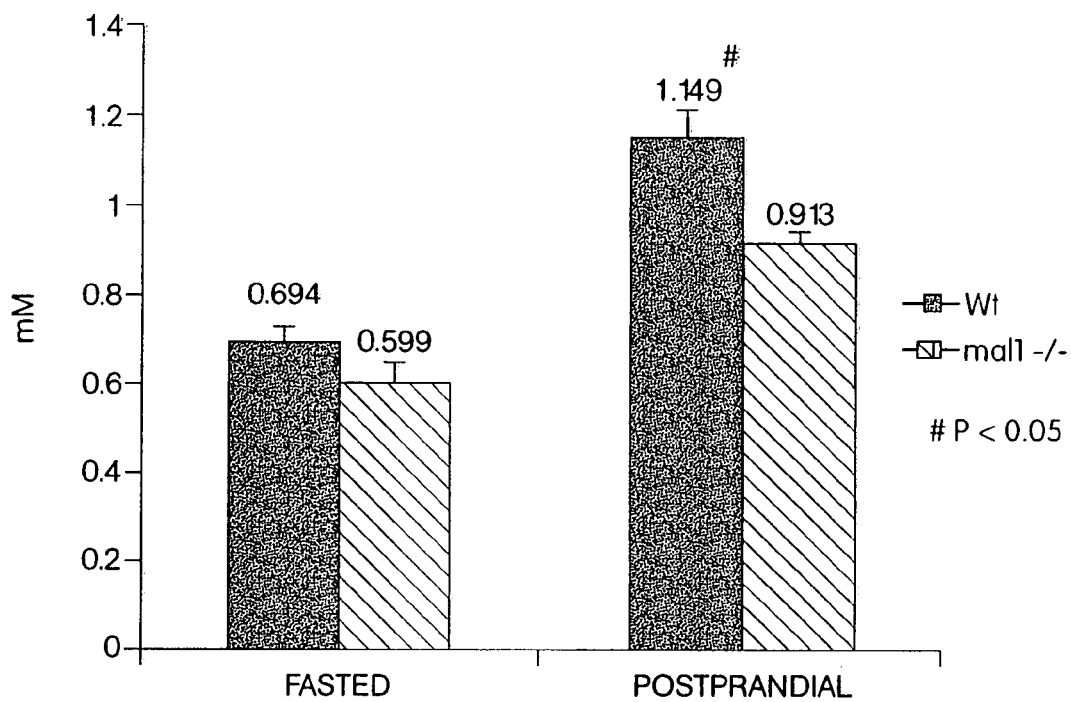
FIG. 8 is a bar graph showing plasma glycerol levels in wild type and mal1-/-mice in a fasted state compared to a postprandial state.
Figure 9:
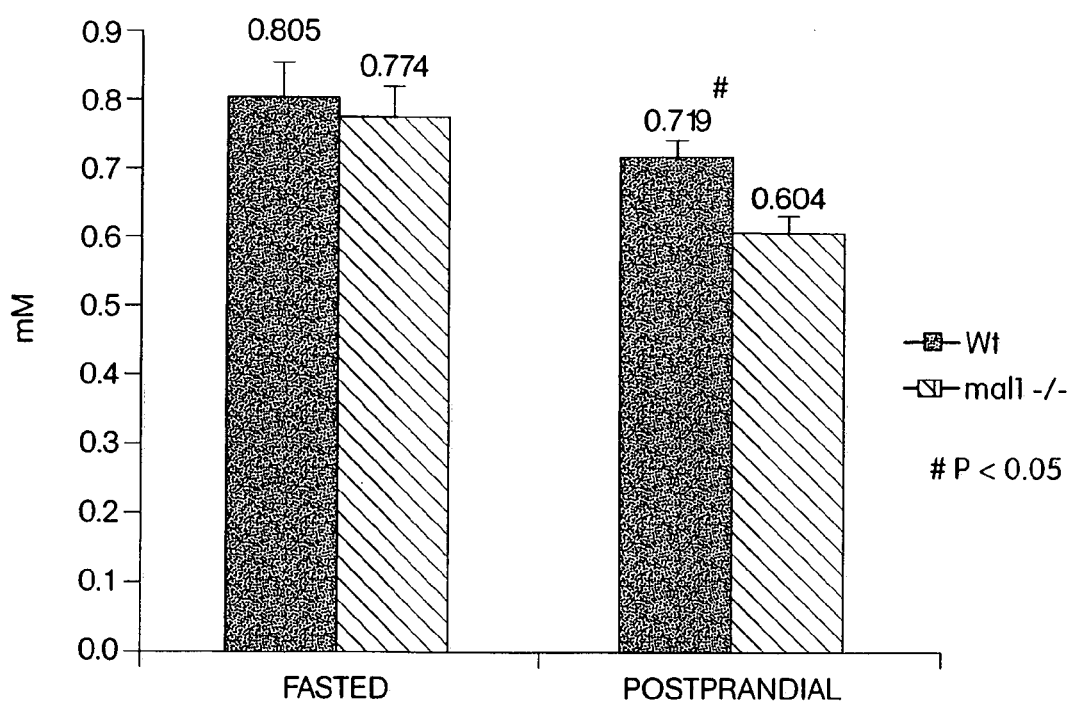
FIG. 9 is a bar graph showing plasma free fatty acid (FFA) levels in wild type and mal1-/-mice in a fasted state compared to a postprandial state.

Lipid metabolism in wild type and mutant mice was evaluated. Plasma from mice in a fasted state and a postprandial state (i.e., following a meal) were analyzed. A decrease in Mal1 expression (mal1-deficient mice; solid bars) led to a lower level of plasma triglycerides and cholesterol compared to mice with normal levels of Mal1 expression (FIGS. 6–7). Plasma glycerol and FFA were also reduced in mice with decreased Mal1 expression (FIGS. 8–9). Plasma triglycerides in Mal1-deficient mice were reduced by 30–40%, and plasma cholesterol was reduced by 15–20% compared to wild type mice.

These data indicate that inhibitors of mal1 are useful to assist in achieving weight loss in obese individuals. Reducing circulating FFA by inhibiting Mal1 is used to prevent or inhibit the development of diabetes. The amount of circulating FFA is measured using methods known in the art.

Expression of Mal1 in Macrophages

Figure 10A:
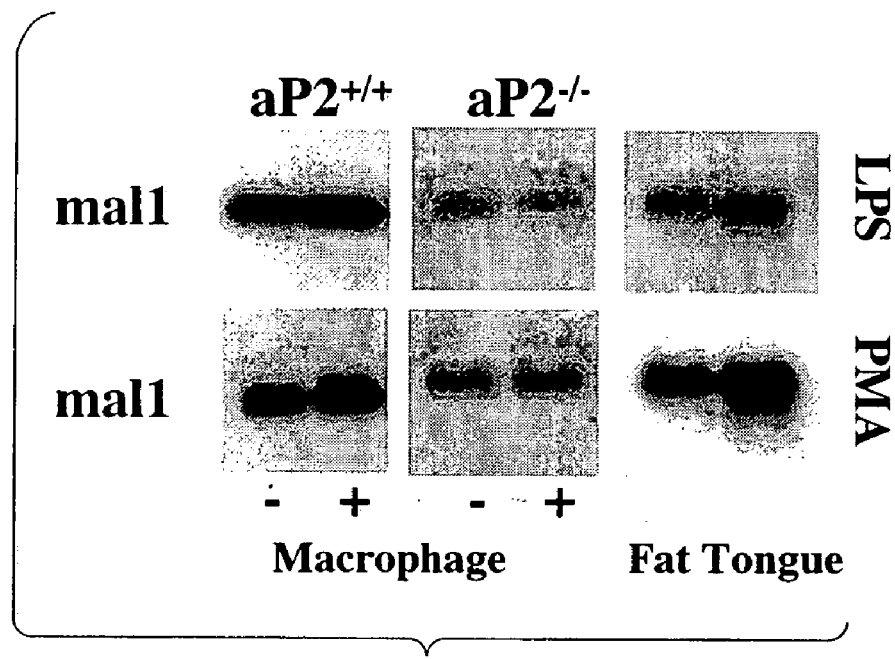
FIG. 10A is a photograph of a northern blot assay showing expression of Mal1 in primary mouse macrophages.
Figure 10B:
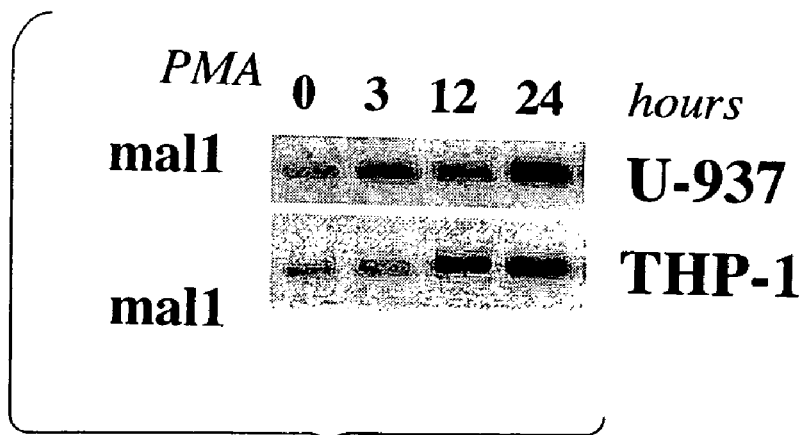
FIG. 10B is a photograph of a northern blot assay showing expression fo Mal1 in human macrophages.

Mal1 was found to expressed in the monocyte/macrophage lineage of cells. Expression was found to increase upon exposure to inflammatory stimuli Macrophages were cultured and treated with lipopolysaccharide (LPS) or phorbol myristate acetate (PMA). Mal1 expression was monitored by northern blot analysis. FIG. 10A shows Mal1 expression in primary mouse macrophages in the presence and absence of inflammatory stimuli (LPS and PMA), and FIG. 10B shows Mal1 expression in two human cell lines (U937, human macrophage cell line; THP-1, human monocyte/macrophage cell line). The results indicate that Mal1 transcription is upregulated after the cells are exposed to inflammatory stimuli. The data also suggest that Mal1 expression is developmentally regulated; the level of expression increases as the cells differentiate from a monocyte phenotype to a macrophage phenotype.

Identification of Compounds which Inhibit Mal1 Expression or Activity

Compounds that inhibit Mal1 expression or activity (thereby inhibiting development of atherosclerosis) are identified by methods ranging from rational drug design to screening of random compounds. The screening of compounds for the ability to Mal1 transcription are carried by identifying compounds that block the binding of trans-acting factors to Mal1 promoter sequences. A 5' regulatory region of the Mal1 gene is linked to a functional promoter and a reporter gene, e.g., the gene encoding luciferase or alkaline phosphatase, and expression assays in the presence and absence of candidate inhibitory compounds are carried out using known methods. For identification of macrophage-specific inhibitors, the expression assays are carried out in macrophages (or in the presence of macrophage lysates) and the level of expression (in the presence and absence of a candidate compound) compared to the level of expression in adipocytes under the same conditions. For luciferase constructs, the cells harboring the construct are harvested after exposure to the candidate compound and luciferase activity measured; for alkaline phosphatase constructs, the culture medium of the cells is collected and the amount of alkaline phosphatase secreted by the cells into the medium is measured.

Antibodies which bind to a Mal1 polypeptide using methods known in the art. Antibodies or other ligands, e.g., a polypeptide or organic molecule, are screened for binding to Mal1 using standard methods. For example, a standard ELISA-type assay may be used. A Mal1 polypeptide is immobilized on a plastic culture vessel and antibodies or other ligands are allowed to bind to the immobilized polypeptide. Bound antibody or ligand is detected using a radioactive or visual, e.g., colorimetric, marker.

Therapeutic Administration

Antisense treatment is carried out by administering to a mammal such as a human patient, DNA containing a promoter, e.g., a macrophage-specific promoter, operably linked to a DNA sequence (an antisense template), which is transcribed into an antisense RNA Antisense treatment is carried out by administering to a mammal such as a human patient, DNA containing a promoter, e.g., a macrophage-specific promoter, operably linked to a DNA sequence (an antisense template), which is transcribed into an antisense RNA. For example, the promoter of the scavenger receptor A gene (Horvai et al., 1995, Proc Natl Acad Sci USA 92:5391–5) is operably linked to a mall antisense template to target expression to macrophages.

The antisense oligonucleotide may be a short nucleotide sequence (generally at least 10, preferably at least 14, more preferably at least 20 (e.g., at least 30), and up to 100 or more nucleotides) formulated to be complementary to a portion, e.g., the coding sequence, or all of Mal1 mRNA. Standard methods relating to antisense technology have been described (see, e.g., Melani et al., 1991, Cancer Res. 51:2897–2901). Following transcription of a DNA sequence into an antisense RNA, the antisense RNA binds to its target nucleic acid molecule, such as an mRNA molecule, thereby inhibiting expression of the target nucleic acid molecule. For example, an antisense sequence complementary to a portion or all of Mal1 mRNA is used to inhibit the expression of Mal1 to reduce macrophage-mediated atherosclerotic lesion formation. Oligonucleotides complementary to various sequences of Mal1 mRNA can readily be tested in vitro for their ability to decrease production of Mal1, using assays described herein. Methods for therapeutically administering antisense oligonucleotides are known in the art, e.g., as described in the following review articles: Le Doan et al., Bull. Cancer 76:849–852, 1989; Dolnick, Biochem. Pharmacol. 40:671–675, 1990; Crooke, Annu. Rev. Pharmacol. Toxicol. 32, 329–376, 1992. Antisense nucleic acids may be used alone or combined with one or more materials, including other antisense oligonucleotides or recombinant vectors, materials that increase the biological stability of the oligonucleotides or the recombinant vectors, or materials that increase the ability of the therapeutic compositions to penetrate vascular smooth muscle cells selectively.

Therapeutic compositions include peptides or antibodies which bind to endogenous Mal1, thereby preventing Mal1 activity, e.g., binding to a fatty acid molecule. Compositions are administered in pharmaceutically acceptable carriers (e.g., physiological saline), which are selected on the basis of the mode and route of administration and standard pharmaceutical practice. Therapeutic compositions include inhibitory proteins or peptides in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic.

Suitable pharmaceutical carriers, as well as pharmaceutical necessities for use in pharmaceutical formulations, are described in Remington's Pharmaceutical Sciences, a standard reference text in this field, and in the USP/NF. A therapeutically effective amount is an amount which is capable of producing a medically desirable result in a treated animal. As is well known in the medical arts, dosage for any one patient depends upon many factors, including the patient's size, body surface area, age, the particular compound to be administered, sex, time and route of administration, general health, and other drugs being administered concurrently. Dosages may vary, but a preferred dosage for intravenous administration of DNA is approximately $10^6$ to $10^{22}$ copies of the DNA molecule.

Mal1 inhibitors are administered to a patient by any appropriate method for the particular compound, e.g., orally, intravenously, parenterally, transdermally, transmucosally Therapeutic doses are determined specifically for each peptide or nonpeptide Mal1 inhibitory compound. For non-nucleic acid type compounds, doses are within the range of 0.001 to 100.0 mg/kg body weight or within a range that is clinically determined to be appropriate by one skilled in the art. The compositions of the invention may be administered locally or systemically. Administration will generally be parenterally, e.g., intravenously.

Methods of Diagnosis

Disease states such as insulin resistance, diabetes, dyslipidemia, atherosclerosis, obesity or predispositions thereto are diagnosed by measuring the level of Mal1 transcripts (e.g., mRNA) in macrophages or by measuring the level of Mal1 protein in the cells. A normal control is the level in macrophages derived from a mammal, e.g., a human patient, known not to be afflicted with the disease in question. A normal control may also be a baseline or average value derived from test results using a pool of normal values. An increase (e.g., 5%, 10%, 20%, 50% or more) in the amount of Mal1 transcript or polypeptide detected in a tissue sample (e.g., peripheral blood) compared to a normal control value indicates that the mammal from which the tissue sample was derived has or is at risk of developing insulin resistance, diabetes, dyslipidemia, atherosclerosis, obesity. Patients at risk of developing the disease include those patients who have no other overt symptoms but have a family history of the disease.

Methods of diagnosis also include detecting a mutation in the Mal1 gene sequence. Nucleic acid is extracted from cells of a patient-derived tissue sample and analyzed. A difference in the sequence compared to the normal control sequence (e.g., SEQ ID NO:2 or 4) indicates a diagnosis of insulin resistance, diabetes, dyslipidemia, atherosclerosis, or a predisposition to developing one or more of the disease states. Methods for detecting mutations, e.g., point mutations, insertions, or deletion) are well-known in the art. For example, mutations are detected by polymerase chain reaction or sequencing methodogies.

Other embodiments are within the following claims.

What claimed is:

1. A method of diagnosing a risk of developing insulin resistance comprising determining the level of a human Mal1 transcript in a tissue sample, wherein an increase of at least 5% in the level of said human Mal1 transcript in said tissue sample compared to a normal control tissue indicates that the human is at risk of developing insulin resistance, wherein said human Mal1 transcript comprises SEQ ID NO:4 or the complement thereof.

2. The method of claim 1, wherein said increase is 10% more than a normal control value.

3. The method of claim 1, wherein said increase is 20% more than a normal control value.

4. The method of claim 1, wherein said increase is 50% more than a normal control value.

5. A method of diagnosing a risk of developing insulin resistance comprising determining the level of a human Mal1 transcript in a tissue sample, wherein an increase of at least 5% in the level of said human Mal1 transcript in said tissue sample compared to a normal control tissue indicates that the human is at risk of developing insulin resistance, wherein said human Mal1 transcript comprises nucleotides 49–456 of SEQ ID NO: 4 or the complement thereof.

6. A method of diagnosing a risk of developing insulin resistance comprising determining the level of a mouse Mal1 transcript in a tissue sample, wherein an increase of at least 5% in the level of said mouse Mal1 transcnpt in said tissue sample compared to a normal control tissue indicates that the mouse is at risk of developing insulin resistance, wherein said mouse Mal1 transcript comprises SEQ ID NO:2 or the complement thereof.

* * * * *

UNITED STATES PATENT AND TRADEMARK OFFICE
CERTIFICATE OF CORRECTION

PATENT NO. : 7,056,662 B2
APPLICATION NO. : 09/788074
DATED : June 6, 2006
INVENTOR(S) : Gokhan S. Hotamisligil It is certified that error appears in the above-identified patent and that said Letters Patent is hereby corrected as shown below:

In claim 6, column 13, line 2, "transcnpt" should read -- transcript --.

Signed and Sealed this

Twenty-eighth Day of November, 2006

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 135
<212> TYPE: PRT
<213> ORGANISM: Mus musculus

<400> SEQUENCE: 1

Met Ala Ser Leu Lys Asp Leu Glu Gly Lys Trp Arg Leu Met Glu Ser
 1               5                  10                  15

His Gly Phe Glu Glu Tyr Met Lys Glu Leu Gly Val Gly Leu Ala Leu
            20                  25                  30

Arg Lys Met Ala Ala Met Ala Lys Pro Asp Cys Ile Ile Thr Cys Asp
        35                  40                  45
```

```
Gly Asn Asn Ile Thr Val Lys Thr Glu Ser Thr Val Lys Thr Thr Val
 50                  55                  60
Phe Ser Cys Asn Leu Gly Glu Lys Phe Asp Glu Thr Thr Ala Asp Gly
 65                  70                  75                  80
Arg Lys Thr Glu Thr Val Cys Thr Phe Gln Asp Gly Ala Leu Val Gln
                 85                  90                  95
His Gln Gln Trp Asp Gly Lys Glu Ser Thr Ile Thr Arg Lys Leu Lys
                100                 105                 110
Asp Gly Lys Met Ile Val Glu Cys Val Met Asn Asn Ala Thr Cys Thr
                115                 120                 125
Arg Val Tyr Glu Lys Val Gln
                130                 135

<210> SEQ ID NO 2
<211> LENGTH: 1279
<212> TYPE: DNA
<213> ORGANISM: Mus musculus

<400> SEQUENCE: 2
aatgggagca acatgctagc tatgcaggtc ggtgagtgag tgagtgagtg acaagaggct     60
ggccagtggg atgataagga atgaatcctt gcttatcatt gtacaaatta cgtcattttc    120
catacccaca ggagtaggac tggctcttag aagatggct gccatggcca agccagactg     180
tatcattacg tgtgatggca acaacatcac ggtcaaaacc gagagcacag tgaagacgac    240
tgtgttctct tgtaacctgg agagaagtt tgatgaaacg acagctgatg cagaaaaac     300 tgaggtcagc tacaacatac tgtgaagcga cagaagcttc tagatttaca gattaaattg    360
cattaacaat gtctgtactt actgccaagg gctgactgaa aaaactactt tatggagttg    420
acttttgata aattagtaaa agtcccagga ctaagaaatg aagacatctt atgagttttct   480 agatcgaaaa gcacatagtt gtattgtgaa caaaatcagt atgatggggt ggagttcaga    540
gagggaaagg cgaagacttg ttggagtggt gtgggtcctg ggggttcctt cactttggaa    600
gatgatgaac taactaccct gtattttgc agacggtctg caccttccaa gacggtgccc     660
tggtccagca ccagcaatgg gacgggaagg agagcacgat aacaagaaaa ctgaaggatg    720
ggaagatgat cgtggtgagc atcaaagcac tggcaccatg ctgggattgg gcctgcagcc    780
acagttgtca taaccacttc gggtcattgg ttctttaaca agagaaggaa acttaggagg    840
acaatactga aataacaag ttagaaacga gagtcctcat tgctgaggca gcccttgtgg     900
ggacggagaa gtgatgggat ccaggatgt ggctgcagca gagcctgaga gctggcaggc     960
caccgagcag ccctctcctg gtacattgat ttaagtaagg gatatttgcc aaaacacatg   1020
aataatttag agatcatatc cagtgcttta gtctgcaggg cagcaaatat acatataaac   1080
aaaacagcag ctctaggtct tcttgagttt gaatcctgag atgtggtttt tctgttaggt   1140
tggttacaag cgtttatagg attctgccca caacacatgc tctgaaatgt acagttggcc   1200
tgagactcta tctttcttct cctaggagtg tgtcatgaac aatgccacct gcactcgggt   1260
ctatgagaag gtgcaatga                                                1279

<210> SEQ ID NO 3
<211> LENGTH: 135
<212> TYPE: PRT
<213> ORGANISM: Homo sapiens
```

-continued

```
<400> SEQUENCE: 3

Met Ala Thr Val Gln Gln Leu Glu Gly Arg Trp Arg Leu Val Asp Ser
  1               5                  10                 15

Lys Gly Phe Asp Glu Tyr Met Lys Glu Leu Gly Val Gly Ile Ala Leu
             20                  25                 30

Arg Lys Met Gly Ala Met Ala Lys Pro Asp Cys Ile Ile Thr Cys Asp
         35                  40                  45

Gly Lys Asn Leu Thr Ile Lys Thr Glu Ser Thr Leu Lys Thr Thr Gln
 50                      55                  60

Phe Ser Cys Thr Leu Gly Glu Lys Phe Glu Glu Thr Thr Ala Asp Gly
 65                  70                  75                  80

Arg Lys Thr Gln Thr Val Cys Asn Phe Thr Asp Gly Ala Leu Val Gln
             85                  90                  95

His Gln Glu Trp Asp Gly Lys Glu Ser Thr Ile Thr Arg Lys Leu Lys
            100                 105                110

Asp Gly Lys Leu Val Val Glu Cys Val Met Asn Asn Val Thr Cys Thr
            115                 120                 125

Arg Ile Tyr Glu Lys Val Glu
        130             135

<210> SEQ ID NO 4
<211> LENGTH: 662
<212> TYPE: DNA
<213> ORGANISM: Homo sapiens

<400> SEQUENCE: 4
accgccgacg cagacccctc tctgcacgcc agcccgcccg cacccaccat ggccacagtt      60
cagcagctgg aaggaagatg gcgcctggtg gacagcaaag gctttgatga atacatgaag     120
gagctaggag tgggaatagc tttgcgaaaa atgggcgcaa tggccaagcc agattgtatc     180
atcacttgtg atggtaaaaa cctcaccata aaaactgaga gcactttgaa aacaacacag     240
ttttcttgta ccctgggaga gaagtttgaa gaaccacag ctgatggcag aaaaactcag      300
actgtctgca actttacaga tggtgcattg gttcagcatc aggagtggga tgggaaggaa     360
agcacaataa caagaaaatt gaaagatggg aaattagtgg tggagtgtgt catgaacaat     420
gtcacctgta ctcggatcta tgaaaaagta gaataaaaat tccatcatca ctttggacag     480
gagttaatta agagaatgac caagctcagt tcaatgagca aatctccata ctgtttcttt     540
cttttttttt tcattactgt gttcaattat ctttatcata aacattttac atgcagctat     600
ttcaaagtgt gttggattaa ttaggatcat cccttggtt aataaataaa tgtgtttgtg      660
ct                                                                   662
```